(12) United States Patent
Harris

(10) Patent No.: US 10,383,331 B2
(45) Date of Patent: Aug. 20, 2019

(54) LIQUID ANTIMICROBIAL COMPRISING A WATER-SOLUBLE POLYMER AND A WATER-SOLUBLE ANTIMICROBIAL AGENT

(71) Applicant: Fantex Limited, Wolverhampton (GB)

(72) Inventor: Keith John Harris, Blackwood (GB)

(73) Assignee: Fantex Limited, Wolverhampton (GB)

(*) Notice: Subject to any disclaimer, the term of this patent is extended or adjusted under 35 U.S.C. 154(b) by 0 days.

(21) Appl. No.: 15/309,532

(22) PCT Filed: Jun. 3, 2015

(86) PCT No.: PCT/GB2015/051614
§ 371 (c)(1),
(2) Date: Nov. 8, 2016

(87) PCT Pub. No.: WO2015/189568
PCT Pub. Date: Dec. 17, 2015

(65) Prior Publication Data
US 2017/0188577 A1 Jul. 6, 2017

(30) Foreign Application Priority Data
Jun. 12, 2014 (GB) .................................. 1410510.0

(51) Int. Cl.
| | | |
|---|---|---|
| A01N 33/12 | (2006.01) | |
| D06M 13/463 | (2006.01) | |
| D06M 15/333 | (2006.01) | |
| A01N 25/10 | (2006.01) | |
| A01N 25/34 | (2006.01) | |
| A01N 47/44 | (2006.01) | |
| D06M 16/00 | (2006.01) | |
| D06M 23/06 | (2006.01) | |
| D06M 101/06 | (2006.01) | |
| D06M 101/32 | (2006.01) | |

(52) U.S. Cl.
CPC ............. *A01N 33/12* (2013.01); *A01N 25/10* (2013.01); *A01N 25/34* (2013.01); *A01N 47/44* (2013.01); *D06M 13/463* (2013.01); *D06M 15/333* (2013.01); *D06M 16/00* (2013.01); *D06M 23/06* (2013.01); *D06M 2101/06* (2013.01); *D06M 2101/32* (2013.01)

(58) Field of Classification Search
None
See application file for complete search history.

(56) References Cited

U.S. PATENT DOCUMENTS

| | | | |
|---|---|---|---|
| 3,429,936 A | 2/1969 | Godt | |
| 3,639,576 A * | 2/1972 | Kaspar | A01N 33/12 134/42 |
| 5,158,766 A * | 10/1992 | Greenwald | A01N 25/24 424/78.33 |
| 5,421,898 A | 6/1995 | Cavanagh | |
| 5,760,088 A | 6/1998 | Walker | |
| 2011/0023240 A1 | 2/2011 | Fossum et al. | |
| 2011/0251285 A1 * | 10/2011 | Tien | A01N 47/44 514/635 |

FOREIGN PATENT DOCUMENTS

| | | | |
|---|---|---|---|
| CA | 947650 A | 5/1974 | |
| CN | 102450275 A | 5/2012 | |
| CN | 103952907 A | 7/2014 | |
| DE | 2917276 A1 | 11/1979 | |
| GB | 2475790 A | 6/2011 | |
| WO | WO-2006081617 A1 | 8/2006 | |
| WO | WO-2007100654 A2 | 9/2007 | |
| WO | WO-2012037615 A1 | 3/2012 | |
| WO | WO-2012146917 A1 | 11/2012 | |
| WO | WO-2013025783 A2 * | 2/2013 | .......... D06M 13/463 |
| WO | WO-2013036996 A1 | 3/2013 | |
| WO | WO-2014060755 A1 | 4/2014 | |
| WO | WO-2014174272 A1 | 10/2014 | |

OTHER PUBLICATIONS

Buck (The Effects of Germicides on Microorganisms; Sep. 1, 2001; http://www.infectioncontroltoday.com/articles/2001/09/infection-control-today-09-2001-the-effects-of-ge.aspx).*
Benzalkonium chloride (https://www.cdc.gov/niosh/ipcsneng/neng1584.html, Jul. 4, 2006) (Year: 2006).*
Habermann, Jörg, "International Search Report," prepared for PCT/GB2015/051614, dated Jul. 22, 2015, six pages.
"Material Safety Data Sheet—Maquat MQ624M," Aug. 1, 2011, pp. 1-5.
Bennett, Edward S., et al.; "Multidose Artificial Tear Products" in: "Clinical Contact Lens Practice"; Lippincott Williams & Wilkins; Jan. 2005; p. 788, Table 41.7.
Japan Vam & Poval Co., Ltd., "Granule (J Series), J-Poval J Series," URL: <http://www.j-vp.co.jp/english/product/pva/pdf/pva01_1.pdf>, Retrieved: May 28, 2019, 2 pages.
International Organization for Standardization, "ISO 20645:2004, Textile Fabrics—Determination of antibacterial activity—Agar diffusion plate test," URL:<htttp://www.iso.org/iso/iso_catalogue/catalogue_tc/catalogue_detail.htm?csnumber=3 5499>, Retrieved: Nov. 7, 2016, 2 pages.
Rowe, Raymond C., et al., "Handbook of Pharmaceutical Excipients," Hydroxyethyl Cellulose, Sixth Edition, Pharmaceutical Press, 2009, pp. 311-314.
Rowe, Raymond C., et al., "Handbook of Pharmaceutical Excipients," Sodium Hydroxide, Sixth Edition, Pharmaceutical Press, 2009, pp. 648-649.
Institute for Occupational Safety and Health of the German Social Accident Insurance, GESTIS Substance Database, Didecyldimethylammonium chloride, URL: <http://gestis.itrust.de/nxt/gateway.dll/gestis_en/000000.xml?f=templates&fn=default.htm&vid=gestiseng:sdbeng>, Retrieved: May 15, 2018, 19 pages.

(Continued)

*Primary Examiner* — Daniel M Podgorski
(74) *Attorney, Agent, or Firm* — Winstead PC

(57) ABSTRACT

This invention relates to a liquid antimicrobial composition comprising: (a) water, (b) a water-soluble polymer, and (c) at least one water-soluble antimicrobial; as well as to an item of clothing, a curtain, a blind, an item of bedding, wallpaper or laundry product comprising the water-soluble polymer and the at least one water-soluble antimicrobial. This invention also relates to a method of preparing the liquid antimicrobial composition comprising the step of mixing water, a water-soluble polymer, and at least one aqueous solution of a water-soluble antimicrobial.

7 Claims, 1 Drawing Sheet

(56) References Cited

OTHER PUBLICATIONS

Sanders, Frank T., "Registration Eligibility Decision for Aliphatic Alkyl Quaternaries (DDAC)," United States Environmental Protection Agency, EPA739-R-06-008, Aug. 2006, 126 pages.
TOXNET, Toxicology Data Network, Didecyl Dimethyl Ammonium Chloride, CASRN: 7173-51-5, Feb. 18, 2015, URL: <https://toxnet.nlm.nih.gov/cgi-bin/sis/search/a?dbs+hsdb:@term+@DOCNO+7611> Retrieved: May 14, 2018, 33 pages.

* cited by examiner

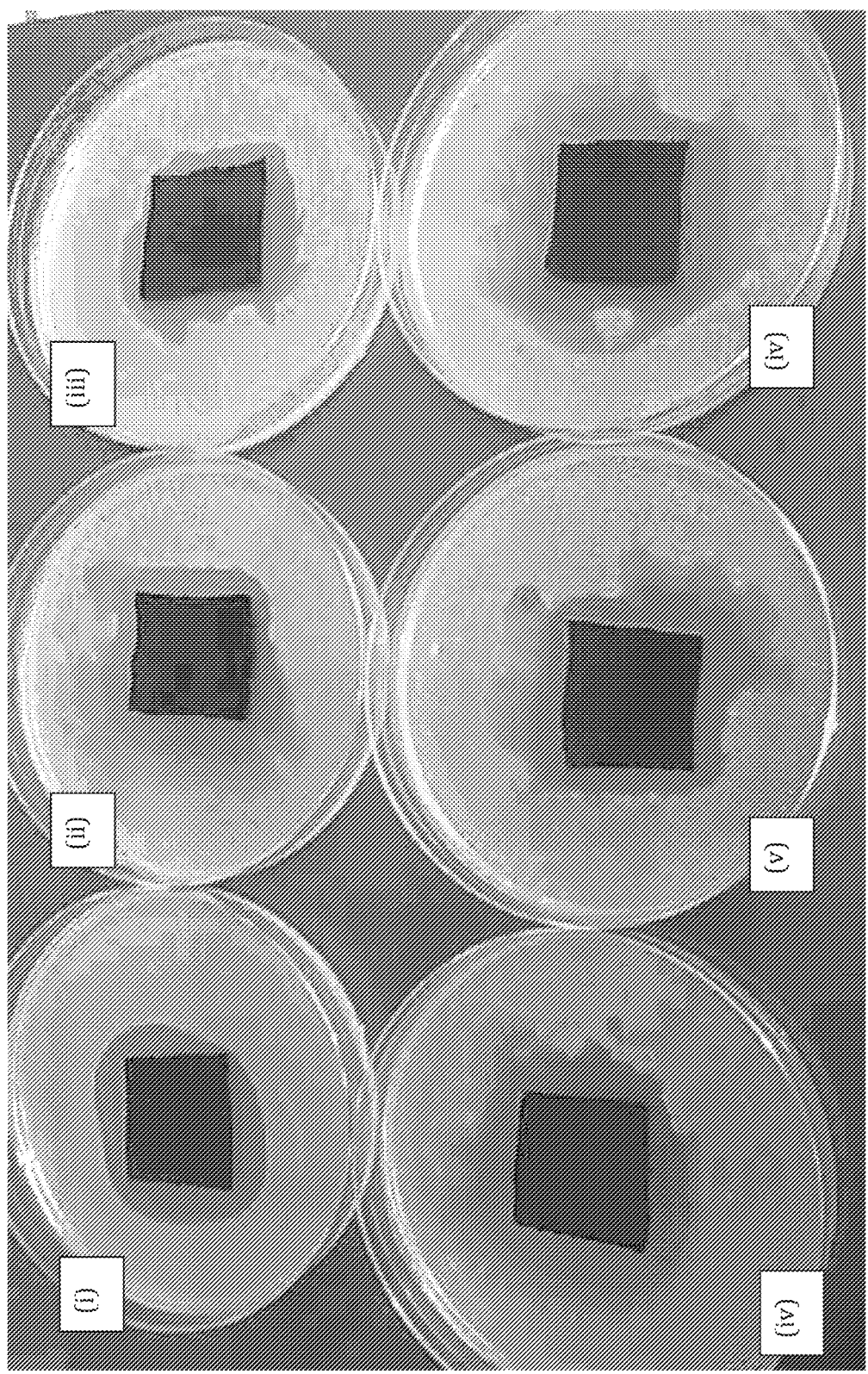

LIQUID ANTIMICROBIAL COMPRISING A WATER-SOLUBLE POLYMER AND A WATER-SOLUBLE ANTIMICROBIAL AGENT

This invention relates to a liquid antimicrobial composition comprising water, a water-soluble polymer and at least one water-soluble antimicrobial. The invention also relates to products incorporating or treated with the liquid antimicrobial composition.

BACKGROUND

It is known to incorporate antimicrobials into consumer products in order to inhibit the growth of, for example, bacteria and/or fungi and/or viruses. For absorbent fabrics such as clothing, curtains/blinds and bedding, antimicrobials can be incorporated by applying a liquid containing the antimicrobial to the fabric, and then allowing the fabric to dry.

A disadvantage of applying antimicrobials in this way is that once the fabric has dried it can have a different feel on the user's skin compared to how the fabric felt to the user before treatment. This is generally considered by users of such fabrics to be unpleasant and undesirable. Thus, this invention seeks to provide a liquid antimicrobial which, when applied to an absorbent fabric which is then dried, more closely retains the original feel of the fabric.

An additional problem with applying antimicrobials to absorbent fabrics as described above is that the antimicrobial will be washed out of the fabric as it is repeatedly laundered. This invention therefore also seeks to provide a liquid antimicrobial that has an increased retention time in absorbent fabrics after repeated laundry cycles.

STATEMENT OF INVENTION

This invention relates to a liquid antimicrobial composition comprising:
(a) water,
(b) a water-soluble polymer, and
(c) at least one water-soluble antimicrobial.

In this way, a liquid antimicrobial is provided which can be applied to absorbent materials. It is believed that, compared to prior art compositions, the inclusion of the water-soluble polymer can provide (i) a reduced detrimental effect to the feel of the fabric, and (ii) an increased retention time in the fabric after repeated laundry cycles.

In relation to this invention, the term "antimicrobial" is used to refer to a substance that can kill microorganisms or inhibit their growth. Examples of antimicrobials include germicides, antibiotics, antibacterials, antivirals and antifungals. It is preferred that the antimicrobial provides up to a log 4 reduction in the number of cells of the microorganism in question. For example, a reduction in the number of cells from $10^8$ to $10^4$ would be a log 4 reduction (ie killing of 99.9% of the cells in question).

It is preferred that the liquid antimicrobial composition comprises:
(a) at least 30 wt % water,
(b) 1-10 wt % of the water soluble polymer, and
(c) 5-69 wt % of the at least one water-soluble antimicrobial.

Preferably, the liquid antimicrobial composition comprises:
(a) 50-60 wt % water,
(b) 3-7 wt % of the water-soluble polymer, and
(c) 35-45 wt % of the at least one water-soluble antimicrobial.

More preferably, the liquid antimicrobial composition comprises:
(a) about 56.5 wt % water,
(b) about 5 wt % of the water-soluble polymer, and
(c) about 38.5 wt % of the at least one water-soluble antimicrobial.

Preferably, the water-soluble polymer is a film forming agent, ie an agent that assists in allowing the composition to form a film (or coating) when it is applied to a substrate.

It is preferred that the water-soluble polymer is a water-soluble polyalkyl alcohol or a polyhexanide, preferably polyhexamethylene biguanide. The water-soluble polyalkyl alcohol is preferably polyvinyl alcohol. Preferably, the polyvinyl alcohol is at least partially hydrolysed, more preferably at least 60 mole % hydrolysed. In a preferred embodiment, the polyvinyl alcohol is 85-93 mole % hydrolysed. Preferably, the polyvinyl alcohol has a viscosity of 10-34 mPa·s as a 4 wt % solution in water at 20° C. Water-soluble polymers, such as polyvinyl alcohol, are particularly preferred because they assist in retaining the water soluble antimicrobial in the fibres of the fabric to which the liquid antimicrobial composition is applied. Without wishing to be bound to any theory, it is believed that this is due to the water-soluble polymer swelling upon contact with water during laundering, helping to lock the antimicrobial into the fibres of the fabric.

It is preferred that the at least one water-soluble antimicrobial is a quaternary ammonium compound. The quaternary ammonium compound is preferably a quaternary ammonium alkyl compound, more preferably benzalkonium chloride or didecyldimethylammonium chloride. It is preferred that when the liquid antimicrobial composition comprises benzalkonium chloride, it is present in an amount of 5-50 wt %. In some embodiments, the amount of benzalkonium chloride is 10-25 wt %, preferably 15-20 wt %, more preferably about 17.5 wt %. It is preferred that when the liquid antimicrobial composition comprises didecyldimethylammonium chloride, it is present in an amount of 10-50 wt %. In some embodiments, the amount of didecyldimethylammonium chloride is 14-28 wt %, preferably 19-23 wt %, more preferably about 21 wt %.

In a preferred embodiment, the at least one water-soluble antimicrobial comprises two water-soluble antimicrobials. The inclusion of two antimicrobials can provide a broader spectrum of antimicrobial activity. The two water-soluble antimicrobials are preferably benzalkonium chloride and didecyldimethylammonium chloride. It is preferred that the liquid antimicrobial composition comprises 15-20 wt % benzalkonium chloride and 19-23 wt % didecyldimethylammonium chloride, more preferably about 17.5 wt % benzalkonium chloride and about 21 wt % didecyldimethylammonium chloride.

Alternative antimicrobials that may be used in the compositions of the invention include 2-bromo-2-nitropropane-1,3-diol; polyhexanides, preferably polyhexamethylene biguanide; and/or chlorophenols, preferably 4-chloro-3,5-dimethylphenol, 2-chloro-3-methyl-phenol, 2,4-dichloro-3,5-dimethylphenol, 2,4-dichloro-5-methylphenol, 4-chloro-3-methylphenol and/or 2,4,6-trichlorophenol.

In some embodiments, the remainder of the liquid antimicrobial composition comprises incidental impurities.

A preferred liquid antimicrobial composition as described above comprises water, 85-93% hydrolysed polyvinyl alcohol, benzalkonium chloride, and didecyldimethylammonium chloride. A particularly preferred composition comprises:
(a) 50-60 wt % water, preferably about 56.5 wt % water,
(b) 3-7 wt % of 85-93% hydrolysed polyvinyl alcohol, preferably about 5 wt % of 85-93% hydrolysed polyvinyl alcohol,
(c) 15-20 wt % benzalkonium chloride, preferably about 17.5 wt % benzalkonium chloride, and
(d) 19-23 wt % didecyldimethylammonium chloride, preferably about 21 wt % didecyldimethylammonium chloride.

This invention also relates to a method of preparing a liquid antimicrobial composition as described above, comprising the step of mixing water, a water-soluble polymer, and at least one aqueous solution of a water-soluble antimicrobial. Preferably, the method comprises the step of mixing 25-35 wt % water, 3-7 wt % of the water-soluble polymer, and 60-70 wt % of the at least one aqueous solution of a water-soluble antimicrobial. More preferably, the method comprises the step of mixing about 30 wt % water, about 5 wt % of the water-soluble polymer, and about 65 wt % of the at least one aqueous solution of a water-soluble antimicrobial. In a preferred embodiment, the method comprises the step of mixing about 30 wt % water, about 5 wt % of the water-soluble polymer, about 35 wt % of a 50 wt % aqueous solution of benzalkonium chloride, and about 30 wt % of a 70 wt % aqueous solution of didecyldimethylammonium chloride.

This invention also relates to a method of applying a liquid antimicrobial composition as described above to an absorbent material, comprising the step of contacting the absorbent fabric with the liquid antimicrobial composition. During the contacting step the liquid antimicrobial composition may be in the form of a liquid and/or a vapour. The absorbent material may be an absorbent fabric. Preferably, the method comprises the step of drying the material after the contacting step. In some embodiments, the amount of liquid antimicrobial composition applied to the absorbent material is 20-100 g/m$^2$, preferably 25-30 g/m$^2$, more preferably about 27 g/m$^2$.

In relation to this invention, the term "absorbent material" is used to mean any material which is capable of absorbing the liquid antimicrobial composition. In relation to this invention, the term "absorbent fabric" (for example a woven fabric such as cotton or a blend of polyester and cotton, or nonwoven fabric such as polypropylene or viscose) is used to mean a fabric or cloth which is capable of absorbing the liquid antimicrobial composition. The absorbent material may be an item of clothing, a curtain, a blind, an item of bedding, wallpaper or laundry product. Examples of items of clothing include t-shirts and socks. Examples of items of bedding include pillows and duvets.

This invention also relates to an item of clothing, a curtain, a blind, an item of bedding, wallpaper or laundry product comprising a water-soluble polymer and at least one water-soluble antimicrobial as described above. Examples of items of clothing include t-shirts and socks. Examples of items of bedding include pillows and duvets. The composition of the invention can be particularly useful in inhibiting the growth of fungi on the dead skin that accumulates in bedding. Bedbugs are known to feed on these fungi, so inhibiting its growth reduces the viability of the bedbugs. Examples of laundry products include a liquid formulation for use during or after a laundry cycle.

This invention will be further described by reference to the following FIGURE which is not intended to limit the scope of the invention claimed, in which:

FIG. 1 shows a photograph of testing of the antibacterial activity of the composition of the invention after various number of washing cycles.

EXAMPLE

A liquid antimicrobial composition was prepared by mixing (a) about 30 wt % water, (b) about 5 wt % of 85-93% hydrolysed polyvinyl alcohol, (c) about 35 wt % of a 50 wt % aqueous solution of benzalkonium chloride, and (d) about 30 wt % of a 70 wt % aqueous solution of didecyldimethylammonium chloride. This composition was then applied to a polycotton blend t-shirt by spraying, in an amount of around 28 g/m$^2$.

A portion of the treated t-shirt was removed i.e. after 0 washes. The treated t-shirt was then washed 10 times in a 1% solution of a biological laundry detergent at 40° C. after which a sample was removed i.e. 10 washes. This procedure was repeated to give samples after 20, 30, 40 and 50 washes.

The unwashed and washed t-shirt samples were then sterilised at 121° C. for 5 minutes and then tested for antibacterial activity as detailed below.

Evaluation of Antimicrobial Protection

Test species: *Staphylococcus aureus* (ATCC 6538)

Testing was carried out according to EN ISO 20645: 2004—Determination of antibacterial activity—agar diffusion plate test.

A lower layer, 10 ml of culture media (trypticase soy agar, TSA), was poured into sterile Petri dishes and allowed to set. Culture media (TSA), pre-cooled to approximately 45° C., was inoculated with the test bacteria and poured over the lower layer to form an upper layer and allowed to set.

Swatches 25×25 mm of the t-shirt samples were aseptically transferred onto the two-layer agar plates and incubated at 35° C. for 24 hours.

The level of antibacterial activity was assessed by examining the extent of the bacterial growth in the contact zone between the agar and the test swatch. Inhibition zones were calculated using the following formula:

$$H=(D-d)/2$$

Where H is the inhibition zone in mm

D is the total diameter of the swatch and the inhibition zone d is the diameter of the swatch in mm The results of this testing are shown in Table 1 below.

TABLE 1

| SAMPLE | Width of clear zone of no growth | Bacterial growth under swatch | Description | Conclusion |
|---|---|---|---|---|
| 0 wash | 42 mm | No growth | ≥1 mm no growth | Effective |
| 10 washes | 42 mm | No growth | ≥1 mm no growth | Effective |
| 20 washes | 39 mm | No growth | ≥1 mm no growth | Effective |
| 30 washes | 40 mm | No growth | ≥1 mm no growth | Effective |
| 40 washes | 40 mm | No growth | ≥1 mm no growth | Effective |
| 50 washes | 40 mm | No growth | ≥1 mm no growth | Effective |

According to the EN ISO 20645, standard inhibition zones≥1 mm and no growth under the specimen are accepted as effective. 0 mm inhibition and slight growth are evaluated as limited effect.

A photograph of the Petri dishes used in this testing is shown in FIG. 1. The samples are labelled as follows:
(i) 0 washes
(ii) 10 washes
(iii) 20 washes
(iv) 30 washes
(v) 40 washes, and
(vi) 50 washes.

Test results indicate that even after 50 washes the treated t-shirt swatches demonstrated effective antibacterial protection.

The invention claimed is:

1. A liquid antimicrobial composition comprising:
    (a) water;
    (b) a water-soluble polymer; and
    (c) two water-soluble antimicrobials,
    wherein the water-soluble polymer is polyvinyl alcohol,
    wherein the polyvinyl alcohol is 85-93% hydrolysed, and
    wherein the two water-soluble antimicrobials are benzalkonium chloride and didecyldimethylammonium chloride.

2. The liquid antimicrobial composition as claimed in claim 1, comprising:
    (a) 50-60 wt % of the water;
    (b) 3-7 wt % of the water-soluble polymer; and
    (c) 35-45 wt % of the two water-soluble antimicrobial.

3. The liquid antimicrobial composition as claimed in claim 1, wherein the polyvinyl alcohol is 86-89% hydrolysed.

4. The liquid antimicrobial composition as claimed in claim 1, comprising 15-20 wt % benzalkonium chloride and 19-23 wt % didecyldimethylammonium chloride.

5. A method of preparing a liquid antimicrobial composition as claimed in claim 1, the method comprising the step of mixing water, a water-soluble polymer, and at least one aqueous solution of two water-soluble antimicrobials.

6. A method of applying a liquid antimicrobial composition as claimed in claim 1 to an absorbent material, the method comprising the step of contacting the absorbent fabric with the liquid antimicrobial composition.

7. An item of clothing, a curtain, a blind, an item of bedding, wallpaper or laundry product comprising a water-soluble polymer and at least two water-soluble antimicrobials as claimed in claim 1.

* * * * *